US008624191B2

(12) United States Patent
Franke et al.

(10) Patent No.: US 8,624,191 B2
(45) Date of Patent: Jan. 7, 2014

(54) MEASURING DEVICE AND METHOD FOR ANALYZING THE LUBRICANT OF A BEARING

(75) Inventors: Joerg Franke, Hessdorf (DE); Joachim Hering, Wuerzburg (DE); Martin Kram, Gerolzhofen (DE); Joachim Schleifenbaum, Niederwerrn (DE); Alexander Weiss, Chemnitz (DE); Gerhard Roehner, Hemsbach (DE); Sven Floesser, Weinheim (DE); Marcel Schreiner, Mannheim (DE); Thomas Otto, Taura (DE); Thomas Gessner, Chemnitz (DE)

(73) Assignee: Schaeffler Technologies AG & Co. KG, Herzogenaurach (DE)

( * ) Notice: Subject to any disclaimer, the term of this patent is extended or adjusted under 35 U.S.C. 154(b) by 81 days.

(21) Appl. No.: 12/676,486

(22) PCT Filed: Aug. 27, 2008

(86) PCT No.: PCT/DE2008/001432
§ 371 (c)(1),
(2), (4) Date: Mar. 31, 2010

(87) PCT Pub. No.: WO2009/030202
PCT Pub. Date: Mar. 12, 2009

(65) Prior Publication Data
US 2010/0208241 A1 Aug. 19, 2010

(30) Foreign Application Priority Data
Sep. 6, 2007 (DE) .......................... 10 2007 042 254

(51) Int. Cl.
*G01J 5/02* (2006.01)

(52) U.S. Cl.
USPC .................................. 250/339.11; 250/338.1

(58) Field of Classification Search
USPC ...................... 250/338.1, 339.11; 356/51, 70
See application file for complete search history.

(56) References Cited

U.S. PATENT DOCUMENTS

| | | | | |
|---|---|---|---|---|
| 3,777,127 A | * | 12/1973 | Goetchius et al. | 702/25 |
| 5,548,393 A | * | 8/1996 | Nozawa et al. | 356/70 |
| 5,884,494 A | * | 3/1999 | Okoren et al. | 62/126 |
| 6,061,139 A | * | 5/2000 | Takezawa et al. | 356/407 |
| 2002/0079451 A1 | * | 6/2002 | Droessler et al. | 250/339.11 |
| 2003/0193028 A1 | * | 10/2003 | Webster | 250/339.07 |
| 2004/0235686 A1 | * | 11/2004 | Boons et al. | 508/460 |
| 2006/0128025 A1 | | 6/2006 | Banavali | |
| 2010/0157304 A1 | * | 6/2010 | Takahashi et al. | 356/442 |

FOREIGN PATENT DOCUMENTS

| | | |
|---|---|---|
| DE | 3510408 A1 | 10/1986 |
| DE | 9311938 U1 | 10/1993 |
| EP | 0658757 A1 | 6/1995 |

(Continued)

*Primary Examiner* — Marcus Taningco
(74) *Attorney, Agent, or Firm* — Lucas & Mercanti, LLP

(57) ABSTRACT

A measuring device for analyzing a lubricant of a bearing. The measuring device has an electromagnetic radiation emitter, a receiving element and a test area that is arranged between the emitter and the receiving element. The measuring device allows for current information on the condition of the lubricant in the bearing to be obtained. At least some sections of the test area are inside the bearing and the receiving element supplies a spectrum of electromagnetic radiation captured by the test area. Also, a bearing and a seal for the bearing and a method for detecting and monitoring the condition of the lubricant of a bearing.

20 Claims, 1 Drawing Sheet

(56) References Cited

FOREIGN PATENT DOCUMENTS

| EP | 0706050 | A1 | 4/1996 |
|---|---|---|---|
| EP | 1980840 | A1 | 10/2008 |
| WO | 03030621 | | 4/2003 |
| WO | 2007083520 | A1 | 7/2007 |
| WO | WO 2007083520 | A1 * | 7/2007 |

* cited by examiner

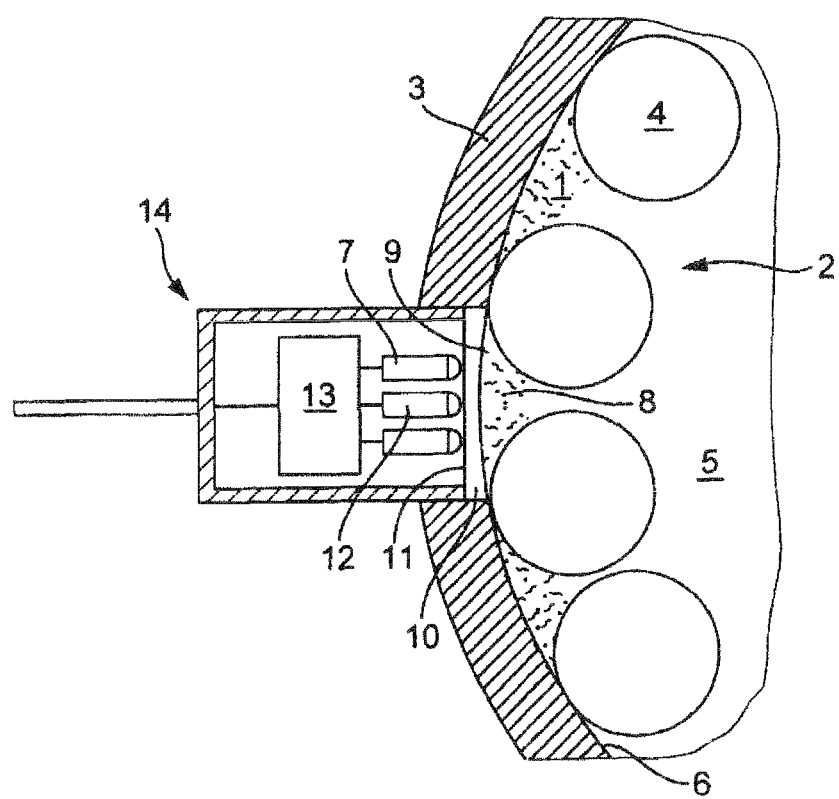

MEASURING DEVICE AND METHOD FOR ANALYZING THE LUBRICANT OF A BEARING

This application is a 371 of PCT/DE2008/001432 filed Aug. 27, 2008, which in turn claims the priority of DE 10 2007 042 254.9 filed Sep. 6, 2007, the priority of both applications is hereby claimed and both applications are incorporated by reference herein.

FIELD OF THE INVENTION

The invention relates to a measurement apparatus for the analysis of a lubricant of a bearing, in particular of a roller bearing or journal bearing, to a bearing, to a seal for a bearing, and to a method for detection and monitoring of the state of a lubricant of a bearing, in particular of a roller bearing or journal bearing.

BACKGROUND OF THE INVENTION

It is known from practice to detect and monitor the state of a lubricant of a bearing, in particular of a roller bearing or journal bearing, and specifically the chemical composition of the lubricant. Changes in the chemical state of the lubricant provide indications of aging processes in the lubricant and indicate when the lubricant must be replaced or replenished.

Within the scope of this application, a "lubricant" is any lubricating substance which is used for lubrication in a bearing, reduces friction and wear and, in some cases, can also be used to carry out further functions, for example for power transmission between the bearing components, for cooling of the bearing, as corrosion protection, for vibration damping, or else as a sealant.

It is known for capacitance measurements to be carried out on the lubricant. However, in this case, layer thicknesses have a major influence on the measurement result. Furthermore, it has been found that the measurement results are widely scattered and are difficult to reproduce. In addition, capacitance measurements provide only an indirect indication of the chemical composition of the lubricant, for example, the measurement results of capacitance measurements are influenced by metallically conductive particles located in the lubricant.

It is also known for a sample of the lubricant to be taken from the bearing and to be irradiated by means of electromagnetic radiation, in order to record and to analyze a spectrum of the sample. Particularly known is the IR-spectroscopic analysis of lubricant grease samples outside the bearing, in the spectral range of the middle and/or near infrared (MIR and NIR). The measurement is carried out outside the bearing, that is to say not subject to the specific physical or chemical constraints in the bearing interior. Furthermore, it is complex to take samples, particularly if access to the bearing is difficult and/or the bearing must be shut down for the sample to be taken. Furthermore, the location within the bearing at which the sample has been taken has an influence on the measurement result of the spectroscopy, since the lubricant is a mixture of components which are distributed within the bearing interior during operation of the bearing. Another problem that has been found is that the lubricant ages to a different extent at different locations within the bearing.

DE 35 10 408 A1 describes an apparatus for monitoring the operating state of bearings. In this case, the instantaneous state of the lubricant of the bearing is determined by providing a trapping device in the immediate vicinity of the bearing, which traps and analyzes lubricant emerging from the bearing. The analysis is restricted to verification of metallic particles which are contained in the lubricant of the bearing, and to the detection of the temperature of the lubricant. No provision is made for any statement relating to the chemical composition of the lubricant in the interior of the bearing.

DE 93 11 938 U1 describes an apparatus for taking a sample of lubricant, in particular lubricating grease, from a roller bearing. In this case, bores are introduced into the bearing rings of the roller bearing, through each of which lubricating grease samples can be taken. In this case as well, immediate in-situ measurement of the state of the lubricant is impossible.

OBJECT OF THE INVENTION

The object of the invention is to specify a measurement apparatus of the type mentioned initially for a bearing, which apparatus allows real-time information to be obtained about the state of the lubricant located in the bearing.

SUMMARY OF THE INVENTION

According to the invention, this object is achieved for the measurement apparatus mentioned initially for a bearing and for a seal for a bearing and facilitates an exemplary implementation of a method for detection and monitoring of the state of the lubricant of the bearing.

Because the sample area is arranged in the interior of the bearing, there is no need for time-consuming taking of samples; in fact, it offers the opportunity to measure the lubricant in situ, that is to say in the physical or chemical conditions of the bearing interior. This avoids the measurement result being corrupted when samples are taken, and are subsequently transported to the analysis unit.

The bearing can be monitored continuously during its operation; this monitoring can be carried out in an automated form, for example with an alarm being triggered as soon as the detected spectra depart from a predetermined norm.

The recording of spectra of the electromagnetic radiation originating from the sample quickly provides information about the chemical state of the lubricant. The electromagnetic radiation does not itself influence or change the lubricant; in addition, in contrast to frequent sampling, there is no longer any loss of lubricant which must be replaced. The spectrum itself provides chemical information about the composition of the lubricant, which is largely independent of foreign bodies such as particles contained in the lubricant.

The sample area is preferably arranged on an inner wall of the bearing, in particular on a section of the inner wall of the bearing which is mechanically loaded and for which lubrication is imperative, in order to allow and to maintain the functionality of the bearing. In the case of roller bearings, it is advantageous, for example, to arrange the sample area in the raceway or in the immediate vicinity of the raceway of the roller bodies on one of the two bearing rings, since exactly in the contact zone between the roller bodies and the bearing ring lubrication is required. The arrangement of the sample area is a governing factor for direct information about the actual state of the lubricant; in addition, it is also possible to detect the situation in which there is no longer any lubricant present, or in any case not or no longer where the lubricant is required.

It is preferable for reflection, in particular total internal reflection, of the electromagnetic radiation emitted from the transmitter to take place in the sample area. In this case, the reflection spectrum, for example the spectrum in the case of diffuse reflection or the spectrum in the case of total internal reflection, provides the information about the chemical composition of the lubricant. Reflection or total internal reflection as measurement principles for recording spectra has the advantage that it is surface-sensitive and it is possible to reliably detect even only small amounts of the lubricant to be verified. Furthermore, it is possible to prevent electromagnetic radiation from entering the interior of the bearing. In the case of reflection or total internal reflection, it is also possible to arrange the transmitter and receiver adjacent to one another, thus allowing the measurement arrangement to be designed to be physically small.

It is preferable for the transmitter, the receiver and the sample area to be combined to form a physical unit, and for the sample area to comprise a boundary surface to the interior of the bearing, on which reflection or total internal reflection occurs. The physical unit can easily and quickly be fitted to and replaced on the bearing; the contact surface between the physical unit is formed only by the boundary surface, whose geometric design or boundary surface material may be optimized for its function for reflection or total internal reflection of the electromagnetic radiation.

The receiver preferably detects and spectrally analyzes the electromagnetic radiation in the infrared range, in particular in the near or middle infrared range. The measurement apparatus is therefore designed in the form of an IR spectrometer. In this case, it has been found to be advantageous for the IR radiation, in particular in NIR or MIR, to excite molecular vibrations in the lubricant, which provide precise information about the chemical condition of characteristic, IR-active groups in the lubricant; on the other hand, in contrast to UV or X-ray beams, IR-beams do not influence the chemical composition of the lubricant. It is also advantageous that a large number of IR-permeable substances have a refractive index which is considerably greater than 1 in the IR range, in particular in the NIR and MIR range, as a result of which the glancing angle at which total internal reflection occurs on a boundary surface, is not very high. In particular, an IR-beam can be injected into an optically dense medium such that total internal reflection occurs on the boundary surfaces to the optically thin medium, for example the interior of the roller bearing with the lubricant, in which case an evanescent field enters the optically thinner medium, and therefore the lubricant, from the optically denser medium, in such a way that the sample area is located in the interior of the bearing and the optically denser medium, specifically the optically denser medium which is in the form of a type of window, is located outside the interior of the bearing. Since neither the optically denser medium nor other parts of the measurement apparatus extend into the interior of the bearing, these do not interfere with the bearing during operation, but allow measurement of the chemical conditions in the interior of the bearing, specifically a chemical analysis of the state of the lubricant, by means of the evanescent field which extends into the interior of the bearing.

It is particularly preferable for the receiver to detect and analyze the electromagnetic radiation in the region of the combination modes of the C—H vibrations. This takes account of the fact that C—H vibrations, in particular C—H stretching vibrations, have a high absorption coefficient, as a result of which even small amounts or thin layers cause virtually complete absorption in the relevant wavelength range, as a result of which the downstream receiver no longer receives a signal which can be utilized. In the process, especially details of the spectrum, for example the position and strength of individual absorption peaks, drop out for evaluation of the spectrum, as a result of which the information must essentially be restricted to the verification of the C—H bonds as such. The absorption coefficient is considerably lower in the range of the C—H combination modes; details of the spectrum can be identified here and, if appropriate, the thickness of the layer of the lubricant can be deduced from the magnitude of the absorption. In this case, "combination modes" means combination modes in the relatively narrow sense as well as harmonic vibrations. For example, for C—H stretching vibrations, it is feasible to evaluate the C—H combination mode in the range from about 2000 to about 2450 nm, or the first harmonic of said combination mode in the range from about 1350 to about 1450 nm. The range of the first harmonic of the C—H stretching vibration can also be evaluated in the range from about 1630 to about 1800 nm, in the same way as the range of the second harmonic of the C—H stretching vibration in the range from about 1200 nm. Each of the abovementioned combination modes, harmonic of a combination mode or first or harmonic, offers the advantage of only a low absorption coefficient.

The range of the C—H combination modes is therefore particularly appropriate for a method for detection and monitoring the state, specifically the chemical composition, of the lubricant in the bearing. In one preferred embodiment, the method can continuously detect and spectrally analyze the range of the C—H combination modes for a bearing at specific times, for example before starting up the bearing or during the operation of the bearing. The spectra therefore offer a time series whose profile corresponds to the aging and degradation of the lubricant. Changes in the chemical composition of the lubricant are reflected in the time series; for example, there may be provision for relating spectra which have been recorded successively in time to one another or to compare them with the spectrum which was recorded before the bearing was started up. By way of example, said method can be carried out using a measurement apparatus as described above; however, it is self-evident that it is likewise possible to provide for samples of the lubricant to be taken from the bearing and for these to be examined spectroscopically outside the bearing, provided that the spectra are recorded and evaluated in the range of the C—H combination mode.

The transmitter of the measurement apparatus preferably comprises a diode, in particular an IR diode, which is physically small and has no significant losses resulting from heat emission.

Said measurement apparatus can be arranged both in a bearing and in a seal for a bearing. For example, if the bearing is in the form of a roller bearing, the measurement apparatus may be accommodated as a physical unit in a bore in one of the bearing rings of the roller bearing.

Further advantages and features of the invention will become evident from the description of one exemplary embodiment of the invention and from the dependent claims.

The invention will be described and explained in more detail in the following text using one preferred exemplary embodiment and with reference to the attached drawing.

BRIEF DESCRIPTION OF THE DRAWINGS

FIG. 1 shows, schematically, one exemplary embodiment of a measurement apparatus according to the invention, in a section of an exemplary embodiment of a bearing according to the invention.

DETAILED DESCRIPTION OF THE DRAWING

FIG. 1 shows a measurement apparatus for analysis of the chemical composition of a lubricant 1 of a bearing, part of which is illustrated, and which is in the form of a roller bearing 2. The roller bearing 2 comprises an outer ring 3, part of which is illustrated, as well as roller bodies 4 which are arranged in the interior 5 of the roller bearing 2 and roll on a raceway 6 on the inside of the outer ring 3. The lubricant 1 is located at least partly in the area of the raceway 6 for the roller bodies 4.

The measurement apparatus comprises a transmitter 7 which is in the form of IR-diodes, as well as a sample area 8, on an IR-permeable window 10 which forms a boundary surface 9 with the interior 5 of the roller bearing 2. The lubricant 1 lies partially on the boundary surface 9 in the area of the sample area 8. The boundary surface 9 is curved, with the curvature of the boundary surface 9 corresponding to the inside of the outer ring 3 in the area of the raceway 6. The boundary surface 9 represents a section of an inner wall of the roller bearing 2. That area of the boundary surface 9 which is coated with the lubricant 1 and faces the interior 5 of the roller bearing 2 forms the sample area 8, which is interspersed with the IR radiation. The roller bodies 4 cross over from the raceway 6 onto the boundary surface 9 and then again over to the raceway 6, whereby they are conveying lubricant 1 on the boundary surface 9. The lubricant 1 on the boundary surface 9 prevents excessive friction of the roller bodies 4 on the boundary surface 9 and compensates for differences in the coefficient of friction between the area of the raceway 6 and of the boundary surface 9.

The input of the transmitters 7, two of which are illustrated, is coupled to an outward-facing side 11 of the window 10. The transmitters 7 are arranged in an annular shape around a receiver 12. The FIGURE also shows a unit for signal processing 13, which is connected downstream from the receiver 12. In particular, the signal processing may comprise electronic correction of the temperatures amongst which various spectra were recorded, and for this purpose process the signal from a temperature measurement unit, which is not illustrated. The receiver 12 is designed such that it can respond in the NIR and MIR ranges, and can produce a spectrum of the lubricant 9 that is located in the sample area 8. In particular, said spectral range also includes the range of the combination modes of C—H vibrations.

The transmitters 7, the receiver 12 and the window 11 having the boundary surface 9 which is adjacent to the sample area 8 in the interior 5 of the roller bearing 2 form a physical unit 14, which is essentially in the form of a rod and is arranged in a bore in the wall surface of the outer ring 3 such that the boundary surface 9 terminates essentially flush with the inside of the outer ring 3, such that the sample area 8 of the measurement apparatus, that is to say the area between the transmitter 7 and the receiver 12, which area has the sample to be analyzed, is arranged in the interior 5 of the roller bearing 2, specifically on an inner wall of the outer ring 3 of the roller bearing 2.

The invention now functions as follows:

The transmitters 7 transmit electromagnetic radiation which also has a component in the MIR and NIR. The output of the transmitters 7 is coupled to the inside 11 of the window 10, and is reflected back and forth between the inside 11 and boundary surface 9. In this case, the material of the window 10 is chosen such that the beam which is located in the window 10 strikes the boundary surface 9 at an angle of about 45°, thus resulting in total internal reflection. When it is totally internally reflected, the beam does not enter the interior 5 of the roller bearing 2 but, in the area of the lubricant, forms an evanescent field, which decays exponentially as the distance from the boundary surface 9 increases. In the area of the evanescent field, that is to say in the subsection of the interior 5 of the roller bearing 2 which is directly adjacent to the boundary surface 9, the evanescent field is partially absorbed by C—H bonds in the lubricant 1. In particular, the evanescent field covers the sample area 8 in the interior of the roller bearing 2. The field which is received by the receiver 12 on the outward-facing side 11 of the window 10 is thus attenuated by the amount absorbed in the sample area 8.

The receiver 12 analyzes the beam spectroscopically; in this case, virtually complete absorption occurs in the range of the C—H stretching vibration, which does not indicate any spectral details. In the range of the C—H combination modes, individual absorption lines can be seen which make it possible to deduce the chemical composition of the lubricant 1. In particular, the receiver 12 determines a spectrum of the beam passing through the sample area 8 in the range of the combination modes, specifically the second harmonic of the C—H stretching vibration, that is to say for wavelengths of about 1200 nm in the range of the NIR (wavelength range from 800 to 2500 nm; with MIR corresponding to a wavelength range from 2500 to 50 000 nm).

When the receiver 12 records a spectrum at different times, the aging of the lubricant 1 can be tracked spectroscopically, and the state of the lubricant 1 in the interior 5 of the roller bearing 2 can be monitored. On the basis of the intensity of the characteristic absorption lines of the C—H vibrations, and of their combination modes as well, it is possible to determine whether there is sufficient lubricant 1, and furthermore, the chemical composition of the lubricant 1. Changes in the spectra can be determined by comparison of the spectra, for example by matching norm spectra, making it possible to deduce the time when the lubricant 1 will be consumed and/or its chemical composition is changed, and when it must be replaced at the latest.

In the case of the exemplary embodiment described above, the boundary surface 9 of the window 10 was curved, while the outward-facing side 11 of the window 10 was flat. It is self-evident that the boundary surface 9 can likewise be flat and it can be parallel to the outward-facing side 11 of the window 10, such that the reflection of the IR beam in the window 10 takes place between two plane-parallel surfaces 9, 11. An arrangement of the surfaces 9, 11 such as this corresponds to a typical ATR geometry. In this case, "ATR" (attenuated total reflection) means a measurement principle based on frustrated total internal reflection with a sample structure in which a beam is injected into an optically denser material and is totally internally reflected in the optically denser material between boundary surfaces to an optically thinner material, in which case, whenever total internal reflection occurs, a sample, which is located in the area of the optically thinner material adjacent to the boundary surface, is measured. The window 10 with the two plane-parallel surfaces 9, 11 may in this case be arranged in the raceway of the roller bodies 4 or at the side, alongside the raceway of the roller bodies 4, with the latter arrangement offering the advantage that the roller bodies 4 do not mechanically load the window 10, but at the same time, by means of the lubricant which is forced sideways onto the window 10, offers the capability to chemically analyze the lubricant.

In the case of the exemplary embodiment described above, the curved boundary surface 9 terminated essentially with the adjacent inner surface of the outer ring 3. It is self-evident that the boundary surface may be at a distance from the adjacent surface of the outer ring or inner ring, thus creating a depression in which the lubricant can gather, and the lubricant, which is located in the depression, can be chemically analyzed at the window 10, which then has a flat boundary surface 9. The depression may be arranged in the raceway of the roller bodies 4 or—preferably—at the side alongside the raceway of the roller bodies 4, with the roller bodies 4 continuously feeding lubricant into the depression. The sample area 8 is then located in the depression, that is to say in the interior 5 of the roller bearing 2.

In the case of the exemplary embodiment described above, the physical unit 14 which is formed from the transmitter 7, the receiver 12 and the window 10 together with the boundary surface 9 was arranged fixed in a bore in the body of the outer ring 3. It is self-evident that the physical unit 14, or only the window 10 together with the boundary surface 9, may also be displaceably arranged in the bore, for example such that whenever a roller body 4 rolls over the unit 14 or the window 10, this presses away from the interior 5 of the bearing 2 in the bore while, for example, the unit 14 is prestressed by a spring means in the direction of the interior 5 of the bearing 2.

The design described above not only allows ATR measurements, but likewise diffuse reflection measurements. In this case, the transmitters 7 irradiate the sample area 8 through the window 10, with absorption taking place in the lubricating grease, with diffuse reflection. The reflected radiation is gathered in the receiver 12, to be precise with that area of the sample area 8 in particular being evaluated which is immediately opposite the receiver 12. Optics may be provided in the receiver 12, which gather the reflected radiation and focus it onto an evaluation unit.

The invention was explained above with reference to a measurement apparatus which is physically integrated in the roller bearing 2. It is self-evident that the measurement apparatus can likewise be provided for a journal bearing or a joint bearing.

It is likewise self-evident that the measurement apparatus may also be fitted in a seal of a bearing. In this case, it is also possible for the transmitter and/or the receiver to be fastened in the body of the seal. In particular, it is possible for the physical unit comprising the transmitter, the receiver and the window together with the boundary surface to be integrated all together in the body of the seal, such that the sample area is arranged in the interior 5 of the bearing. As an alternative to this, it is possible for said physical unit to be provided in the interior of the bearing, close to the seal and possibly attached to the seal. As another alternative to the two abovementioned arrangements, it is also possible to provide a unit comprising the transmitter and the receiver outside the seal and to provide a light-conducting connection in the body of the seal, such that the radiation of the transmitter is passed through the light-conducting connection into the sample area into the interior 5 of the bearing, and is passed from the interior 5 of the bearing through the light-conducting connection to the receiver, where the chemical analysis of the spectrum is carried out. Said unit may in this case be attachable to the seal, but since it is arranged outside the seal, it is independent of the specific configuration of the seal and is suitable for different types of seals. The fastening of the unit to the seal may be detachable, for example as a clip which is fitted to the bearing seal as required. The light-conducting connection may comprise an optical conductor onto whose outward-facing connections said unit may be detachably plugged in the form of a plug module. It is also self-evident that said options for the arrangement of the transmitter and of the receiver on the seal may also be combined, for example such that the transmitter is arranged internally and the receiver externally on the seal, or such that, although the transmitter is attached to the body of the seal, the receiver may, however, be fitted replaceably to the seal, in particular for the situation in which different spectral ranges can be analyzed by means of the receiver.

Furthermore, it may be provided to arrange an optical conductor between the sample area 8 and the transmitter 7; the transmitter or the transmitters 7 may then be provided outside the bearing. An optical conductor may likewise be provided between the sample area 8 and the receiver 12. The sample area 8 is then formed by the area of the interior 5 of the bearing which is provided between the output of the optical conductor associated with the transmitter 7 and the input of the optical conductor associated with the receiver 12.

It is also self-evident that not just C—H vibrations but also other modes, such as those of water or, more generally, of O—H groups or functional groups of additives, can be detected and analyzed.

Where the above text has referred to "combination modes" it is self-evident that the term "combination modes" is intended to cover not only combination modes in the direct sense but also harmonic vibrations, be these fundamental vibrations or else combination modes.

LIST OF REFERENCE SYMBOLS

1 Lubricant
2 Roller bearing
3 Outer ring
4 Roller body
5 Interior of the roller bearing 2
6 Raceway
7 Transmitter
8 Sample area
9 Boundary surface
10 Window
11 Side of the window 10 pointing outward
12 Receiver
13 Unit for signal processing
14 Physical unit

The invention claimed is:

1. A measurement apparatus for analysis of a lubricant of a hearing, comprising:
    a transmitter of electromagnetic radiation;
    a receiver; and
    a sample area, which is arranged in front of the transmitter and the receiver,
    wherein the sample area is arranged at least in places in an interior of the hearing that is filled with a lubricant, the sample area, the transmitter, and the receiver are configured with a diffuse reflection geometry so that the transmitter irradiates the sample area and the receiver receives diffuse reflection of the electromagnetic radiation from the sample area, and the receiver produces a spectrum of the electromagnetic radiation received by the diffuse reflection from the lubricant in the sample area that is used to measure the deterioration of the lubricant.

2. The measurement apparatus of claim 1, wherein the sample area is arranged on an inner wall of the bearing.

3. The measurement apparatus of claim 1, wherein the sample area, the transmitter, and the receiver are further configured to allow total internal reflection of the electromagnetic radiation emitted from the transmitter in or close to the sample area.

4. The measurement apparatus of claim 1, wherein the receiver detects and spectrally analyzes the electromagnetic radiation in an infrared range.

5. The measurement apparatus of claim 4, wherein the receiver detects and analyzes the electromagnetic radiation in a region of combination modes of C—H vibrations.

6. The measurement apparatus of claim 1, wherein the transmitter is a diode.

7. The measurement apparatus of claim 1, further comprising a light-conducting connection between the transmitter and the sample area.

8. The measurement apparatus of claim 7, wherein the light-conducting connection comprises an optical conductor.

9. The measurement apparatus of claim 1, further comprising a light-conducting connection between the sample area and the receiver.

10. The measurement apparatus of claim 9, wherein the light conducting connection comprises an optical conductor.

11. A bearing, comprising a measurement apparatus for the analysis of the lubricant of the bearing, wherein the measurement apparatus is designed as claimed in claim 1.

12. The bearing of claim 11, wherein the bearing comprises a bearing ring, and at least the sample area of the measurement apparatus is arranged at or adjacent to the bearing ring.

13. The hearing of claim 11, wherein the bearing comprises a bearing seal, and at least the sample of the measurement apparatus is arranged in the bearing seal.

14. A seal for a bearing, comprising a measurement apparatus for the analysis of the lubricant of the bearing, Wherein the measurement apparatus is designed as claimed in claim 1.

15. The seal of claim 14, wherein at least one of the transmitter and the receiver is mounted in a body of the seal.

16. The seal of claim 14, wherein a light-conducting connection is provided in the body of the seal and connects the sample area to at least one of the transmitter and the receiver.

17. The measurement apparatus of claim 1, further comprising a window, which is arranged in front of the transmitter and the receiver, the window having a curved boundary surface that corresponds to a curvature of an inner surface area of an outer ring of the bearing.

18. The measurement apparatus of claim 1, wherein the receiver detects and spectrally analyzes the electromagnetic radiation in a near or a middle infrared range.

19. A method for detection and monitoring of a state of a lubricant of a bearing, comprising the following steps:
- configuring a sample area and a receiver so that the receiver receives, from the sample area, diffuse reflection of electromagnetic radiation emitted by a transmitter, the sample area being arranged at least in places in an interior of the bearing that is filled with a lubricant;
- irradiating, by the transmitter, a sample of the lubricant with electromagnetic radiation;
- detecting, by the receiver from the diffusely reflected electromagnetic radiation, a spectrum of the sample in a range of a C—H combination mode in a near or middle infrared range; and
- using the spectrum to measure a deterioration of the lubricant.

20. The method of claim 19, wherein the spectrum of the sample is detected at different times before starting up and/or during operation of the bearing, and any change in the spectrum in the range of the C—H combination mode is determined.

* * * * *

UNITED STATES PATENT AND TRADEMARK OFFICE
CERTIFICATE OF CORRECTION

PATENT NO. : 8,624,191 B2
APPLICATION NO. : 12/676486
DATED : January 7, 2014
INVENTOR(S) : Franke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 104 days.

Signed and Sealed this
Twenty-second Day of September, 2015

Michelle K. Lee
*Director of the United States Patent and Trademark Office*